(12) United States Patent
Lin et al.

(10) Patent No.: US 8,461,224 B2
(45) Date of Patent: Jun. 11, 2013

(54) SINGLE MONOMER DERIVED LINEAR-LIKE COPOLYMER COMPRISING POLYETHYLENIMINE AND POLY(ETHYLENE GLYCOL) FOR NUCLEIC ACID DELIVERY

(75) Inventors: Shu-Yi Lin, Hsinchu (TW); Chung-Shi Yang, Taichung (TW); Yeu-Kuang Hwu, Taipei (TW)

(73) Assignee: National Health Research Institutes, Miaoli County (TW)

( * ) Notice: Subject to any disclaimer, the term of this patent is extended or adjusted under 35 U.S.C. 154(b) by 103 days.

(21) Appl. No.: 13/041,023

(22) Filed: Mar. 4, 2011

(65) Prior Publication Data
US 2012/0225924 A1    Sep. 6, 2012

(51) Int. Cl.
| | |
|---|---|
| A61K 31/7105 | (2006.01) |
| A61K 31/7052 | (2006.01) |
| C08L 71/02 | (2006.01) |
| C08L 73/00 | (2006.01) |
| C08L 79/02 | (2006.01) |

(52) U.S. Cl.
USPC ............... 522/71; 522/84; 522/178; 523/300; 424/400; 514/45

(58) Field of Classification Search
USPC ............................ 523/300; 522/1, 71, 84, 178
See application file for complete search history.

(56) References Cited

U.S. PATENT DOCUMENTS
6,652,886 B2 * 11/2003 Ahn et al. ..................... 424/501

FOREIGN PATENT DOCUMENTS
WO     WO 02/094005 A2 * 11/2002

OTHER PUBLICATIONS

Lin, Shu-Yi et al. (2010) "One-pot synthesis of linear-like and photoluminescent polyethylenimines for intracellular imaging and siRNA delivery" Chemical Communications 46(30):5554-5556.
Bonnet et al., "Systemic Delivery of DNA or siRNA Mediated by Linear Polyethylenimine (L-PEI) Does Not Induce an Inflammatory Response" Pharmaceutical Research, vol. 25, No. 12, Dec. 2008 (# 2008) DOI: 10.1007/s11095-008-9693-1.
Mao et al. "Influence of Polyethylene Glycol Chain Length on the Physicochemical and Biological Properties of Poly (ethylene imine)-graft-Poly(ethylene glycol) Block Copolymer/SIRNA Polyplexes" Bioconjugate Chem. 2006, 17, 1209-1218.
Tsai et al. "A single-monomer derived Linear-like PEI-co-PEG for siRNA delivery and silencing" biomaterials 2011, 3647-3653.

* cited by examiner

*Primary Examiner* — Richard Schnizer
*Assistant Examiner* — Alma Pipic
(74) *Attorney, Agent, or Firm* — Hisu-Ming Saunders; Intellectual Property Connections, Inc.

(57) ABSTRACT

A method of synthesizing a random copolymer of polyethyleneimine and polyethylene glycol, comprising exposing ethanolamine in a solution to electromagnetic radiation for a sufficient time to polymerize the ethanolamine ($OHCH_2CH_2NH_2$) and thereby resulting in formation of the randome copolymer comprising polyethyleneimine and poly (ethylene glycol), wherein the polyethyleneimine comprises ethyleneimine ($—CH_2CH_2NH—$) unit and the polyethylene glycol comprises ethylene glycol ($—CH_2CH_2O—$) unit, and the polyethylenimine of the random copolymer has a substantially linear backbone.

20 Claims, 5 Drawing Sheets

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: sense oligo for anti-GFP siRNA

<400> SEQUENCE: 1
ggcaagcuga cccugaaguu cuutt                                         25

<210> SEQ ID NO 2

```
<211> LENGTH: 25
<212> TYPE: DNA
<213> ORGANISM: Artificial Sequence
<220> FEATURE:
<223> OTHER INFORMATION: antisense oligo for anti-GFP siRNA

<400> SEQUENCE: 2
aagaacuuca gggucagcuu gcctt                                          25

<210> SEQ ID NO 3
<211> LENGTH: 27
<212> TYPE: DNA
<213> ORGANISM: Artificial Sequence
<220> FEATURE:
<223> OTHER INFORMATION: sense oligo for anti-VEGF siRNA

<400> SEQUENCE: 3
ugaagaugua cucgaucuca ucaggtt                                        27

<210> SEQ ID NO 4
<211> LENGTH: 27
<212> TYPE: DNA
<213> ORGANISM: Artificial Sequence
<220> FEATURE:
<223> OTHER INFORMATION: antisense  oligo for anti-VEGF siRNA

<400> SEQUENCE: 4
ccugaugaga ucgaguacau cuucatt                                        27
```

SINGLE MONOMER DERIVED LINEAR-LIKE COPOLYMER COMPRISING POLYETHYLENIMINE AND POLY(ETHYLENE GLYCOL) FOR NUCLEIC ACID DELIVERY

FIELD OF THE INVENTION

The present invention relates generally to non-viral vectors for nucleic acid delivery, and more specifically to polymer-based vehicles for nucleic acid delivery.

BACKGROUND OF THE INVENTION

Polyethylenimines (PEIs) are promising non-viral vehicles for effective protection and delivery of short/small interfering RNA (siRNA), a therapeutic tool used to knock down mRNA levels, thereby arresting the translation of cancer-related proteins. Not only do PEIs prevent siRNA degradation during transfection, but also their strong buffer capacities allow the PEIs/siRNA complexes to follow an endosome-escape mechanism for mRNA silencing. However, the toxicity of current PEIs-based vehicles is high, and the efficiency of siRNA release is low. Branched PEIs (BPEIs) have been initially demonstrated to act as siRNA-delivery vectors. The transfection efficiency and toxicity of BPEIs, however, are strongly correlated with their molecular weights. BPEIs with high molecular weights display enhanced efficiency but also dramatically increased toxicity. In contrast, linear-like PEIs (LPEIs) exhibit less toxicity and elicit a weaker inflammatory response than BPEIs. Unfortunately, the release efficiency of siRNA from the LPEI-based vehicles is still insufficient.

In the past decade, most researches focused on reducing the cytotoxicity of BPEIs through structure modification, rather than enhancing the release efficiency of LPEIs. Post-modification of BPEIs can significantly decrease their toxicity; various building blocks such as polyethylene glycol (PEG) segments and alkyl groups can attenuate the positive charges of the tertiary amines. Nevertheless, the modified BPEIs still present adverse side effects, such as intracellular stress and mitochondrial alternations leading to cell death. LPEIs are much safer than BPEIs, but current time-consuming synthesis and purification methods limit the use of LPEIs in bio-related applications. Recently, a high-throughput and organic-solvent-free protocol for LPEIs synthesis was developed to overcome these limitations (Shu-Yi Lin, et al., "One-pot synthesis of linear-like and photoluminescent polyethyleneimine for intracellular imaging and siRNA delivery" Chem. Commun. 2010, 46, 5554-5556; and Supplemental materials thereof, both of which are herein incorporated by reference in their entireties).

Therefore, a heretofore unaddressed need exists in the art to address the deficiencies and inadequacies, especially in connection with development of PEIs for efficient delivery and release of siRNA within cells.

SUMMARY OF THE INVENTION

In one aspect, the invention relates to a method of synthesizing a random copolymer of polyethyleneimine and poly(ethylene glycol). The method comprises exposing ethanolamine in a solution to electromagnetic radiation for a sufficient time to polymerize the ethanolamine ($OHCH_2CH_2NH_2$) and thereby resulting in formation of a random copolymer comprising polyethyleneimine and poly(ethylene glycol), wherein the polyethyleneimine comprises ethyleneimine (—$CH_2CH_2NH$—) units and the poly(ethylene glycol) comprises ethylene glycol (—$CH_2CH_2O$—) units, and the polyethylenimine of the random copolymer has a substantially linear backbone.

In another aspect, the invention relates to a composition comprises a random copolymer synthesized by a method as aforementioned.

Further in another aspect, the invention relates to a composition comprising a random copolymer comprising polyethyleneimine and poly(ethylene glycol), the polyethylenimine comprising ethyleneimine (—$CH_2CH_2NH$—) units and the poly(ethylene glycol) comprising ethylene glycol (—$CH_2CH_2O$—) units, wherein the polyethylenimine has a substantially linear backbone.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 2A-2B show $^1$H NMR and $^{13}$C NMR spectra in $D_2O$, respectively, for the $M_2$ (upper panel, star label) and $P_2$ (lower panel).

FIG. 4A shows optical properties of $P_1$ and $P_2$. The profile from left to right showed the absorption spectra (black circle line for $P_1$ and gray circle line for $P_2$) and emission spectra of $P_1$ and $P_2$ (black and gray solid line for $P_1$ and $P_2$, respectively). All measurements were carried out in PBS (15 mM, pH 7.4).

FIGS. 4B1-4C2 show Confocal images. FIGS. 4B1 and 4C1 are two-color imaging of A549 and H460, respectively, in which cells were incubated with $P_2$ and co-stained with a specific-nuclear dye up to 5 min. FIGS. 4B2 and 4C2 are three-color imaging of A549 and H460, respectively, in which cells were co-stained with a nuclear dye and a LysoTracker. Scale bar: 10 μm.

FIG. 8A is a histogram showing GFP green fluorescence intensity in MDA-MB-231 cells after silencing by $P_1$, $P_2$ and Lipofectamine complexes. FIG. 8B is a collection of fluorescence microscopy photographs showing GFP expression in MDA-MB-231 cells after treatment by various conditions: positive control, siRNA alone and three complexes from siRNA/$P_1$, siRNA/$P_2$ and siRNA/Lipofectamine (from left to right) for 48 h. Scale bar: 100 μm. It was noted that Lipofectamine could induce severe cell death under the excellent transfection efficiency.

DETAILED DESCRIPTION OF THE INVENTION

Figure 1:
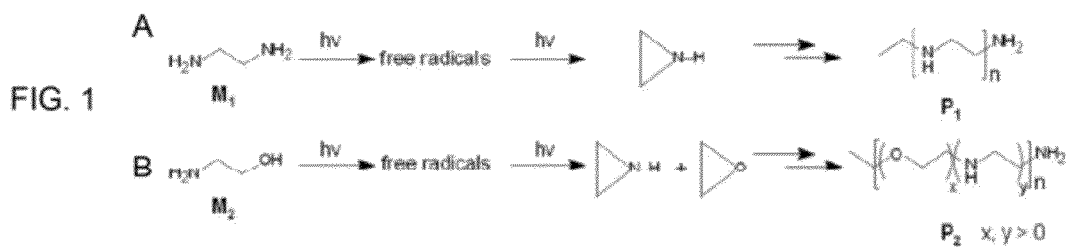
FIG. 1 is a schematic drawing showing a possible mechanism for polymerization of $P_1$ and $P_2$.

The present invention is more particularly described in the following examples that are intended as illustrative only since numerous modifications and variations therein will be apparent to those skilled in the art. Various embodiments of the invention are now described in detail. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

As used herein, a "linear polymer" is a polymer whose molecule is arranged in a chainlike fashion with few branches or bridges between the chains. Linear polyethyleneimine (PEI) contains most or all of secondary amines, in contrast to branched PEIs which contain primary, secondary and tertiary amino groups. The linear PEI is solid at room temperature where branched PEI is liquid at all molecular weights.

The terms Poly(ethyleneimine) and Poly(ethylenimine) are interchangeable.

The term "polydispersity index (PDI)" is a measure of the distribution of molecular weights in a given polymer sample. The PDI calculated is the weight average molecular weight divided by the number average molecular weight. It indicates the distribution of individual molecular weights in a batch of polymers. The PDI has a value always greater than 1, but as the polymer chains approach uniform chain length, the PDI approaches unity (1).

The term "weight average molecular weight" describes the molecular weight of a polymer. Polymer molecules come in different sizes (chain lengths, for linear polymers), thus an average molecular weight is used. A given polymer has a distribution of molecular weights and the distribution depends how it is produced. For polymers, the distribution of molecular weight or of the average molecular weight is usually used. The total weight of polymer divided by the number of polymer molecules is called the number average molecular weight.

The term "statistical copolymers" refers to copolymers in which the sequence of monomer residues follows a statistical rule. If the probability of finding a given type monomer residue at a particular point in the chain is equal to the mole fraction of that monomer residue in the chain, then the polymer may be referred to as a truly random copolymer (e.g., -A-B-B-B-A-B-A-B-A-A-).

The term "block copolymer" refers to a copolymer comprising two or more homopolymer subunits linked by covalent bonds (e.g., -B-B-B-B-B-A-A-A-A-A-). The union of the homopolymer subunits may require an intermediate non-repeating subunit, known as a junction block. Block copolymers with two or three distinct blocks are called diblock copolymers and triblock copolymers, respectively.

The invention relates to discovery of single-monomer derived LPEI-co-PEG ($P_2$) to address the aforementioned problems. The LPEI-co-PEG ($P_2$) was synthesized by synchrotron X-rays (4-30 keV, $10^5$ Gy/s) irradiation, a strong radiation source capable of generating free radicals without extra catalysts and initiators. Briefly, ethanolamine ($M_2$) was introduced into 5 mL of aqueous solution as the monomer (FIG. 1B scheme), and then the mixture was irradiated synchrotron X-rays for approximately 5 min, generating the $P_2$ copolymer with mono-dispersive molecular weight. The x, y and n in FIG. 1B are integers, each represents the number of the repeat of respective units of the random copolymer. It is difficult to calculate the x, y and n values of the random copolymer. Without intent to limit the scope of the invention, for illustration purpose, x, y, n values were estimated as follows by using Mn=1.11 KDa as an example: The ratio of X:Y=1:2. Thus if X=1, Y=2, n=9; if X=2, y=4 n=4; if X=3 y=6 n=3; if X=4 y=8 n=2, and so on.

Additionally, LPEI ($P_1$) was synthesized with an ethylene diamine ($M_1$) monomer using a protocol (FIG. 1A scheme) described in U.S. patent application Ser. No. 12/868,939, which is incorporated herein by reference in its entirety. The reaction was repeated to obtain a control experiment for comparison. $^1$H NMR, $^{13}$C NMR, FT-IR and elemental analysis were used to examine the structure of $P_2$. In addition, the $P_2$ can emit photoluminescence for intracellular tracking as well as LPEI ($P_1$). The release efficiency of the siRNA/LPEI-co-PEG ($P_2$) complexes was investigated and compared to that of the siRNA/LPEI ($P_1$) complexes.

In one aspect, the invention relates to a method of synthesizing a random copolymer of polyethyleneimine and poly(ethylene glycol). The method comprises exposing ethanolamine in a solution to electromagnetic radiation for a sufficient time to polymerize the ethanolamine ($OHCH_2CH_2NH_2$) and thereby resulting in formation of a random copolymer comprising polyethyleneimine and poly(ethylene glycol), wherein the polyethyleneimine comprises ethyleneimine ($—CH_2CH_2NH—$) units and the poly(ethylene glycol) comprises ethylene glycol ($—CH_2CH_2O—$) units, and the polyethylenimine of the random copolymer has a substantially linear backbone.

The reactive solution does not contain organic solvents, acids, free-radical-forming agents, azo initiators, or peroxide initiators, or all of the aforementioned agents.

Without intent to limit the scope of the invention, a polyethylenimine having a substantially linear backbone generally has at least 60% secondary amine in the polyethylenimine.

In one embodiment of the invention, the ethanolamine in the solution is irradiated for no greater than 10 minutes.

In another embodiment of the invention, the random copolymer is formed in the absence of a reagent chosen from organic solvents, acids, catalysts, and poly(alkyl ethylene).

In another embodiment of the invention, the electromagnetic radiation is chosen from X-rays, microwaves, and gamma-rays.

In another embodiment of the invention, the electromagnetic radiation comprises X-rays.

In another embodiment of the invention, the radiation has energy ranging from 3 to 3,000 KeV and a radiation dose ranging from $2\times10^3$ to $10^7$ Gy/s.

By ranging from 3 to 3,000 KeV it meant that all integer unit amounts within the range are specifically disclosed as part of the invention. Thus, 3, 4, 5 . . . 2998, 2999 and 3000 unit amounts are included as embodiments of this invention.

By ranging from $2\times10^3$ to $10^7$ Gy/s it meant that all integer unit amounts within the range are specifically disclosed as part of the invention. Thus, $2\times10^3$, $3\times10^3$, $4\times10^3$ . . . $8\times10^6$, $9\times10^6$ and $10^7$ unit amounts are included as embodiments of this invention.

In another embodiment of the invention, the method further comprises removing the ethanolamine after the formation of the random copolymer.

In another aspect, the invention relates to a composition comprises a random copolymer synthesized by a method as aforementioned.

In another aspect, the invention relates to a composition comprising a random copolymer comprising polyethyleneimine and poly(ethylene glycol), the polyethyleneimine comprising ethyleneimine ($—CH_2CH_2NH—$) units and the poly(ethylene glycol) comprising ethylene glycol ($—CH_2CH_2O—$) units, wherein the polyethylenimine has a substantially linear backbone.

In one embodiment of the invention, the aforementioned random copolymer is peptide free.

In another embodiment of the invention, the aforementioned random copolymer has a weight average molecular weight ranging from 1 kDa to 200 kDa.

By ranging from 1 kD to 200 kDa it meant that all integer unit amounts within the range are specifically disclosed as part of the invention. Thus, 1, 2, 3 . . . 198, 199 and 200 unit amounts are included as embodiments of this invention.

In another embodiment of the invention, the aforementioned random copolymer has a polydisperisty index of greater than 1 but less than 1.9.

By greater than 1 but less than 1.9 it meant that all tenth and integer unit amounts within the range are specifically disclosed as part of the invention. Thus, 1.0, 1.1, 1.2 . . . 1.7, 1.8 and 1.9 unit amounts are included as embodiments of this invention.

In another embodiment of the invention, the random copolymer has an oxygen/nitrogen ratio of between 0.35 and 0.60.

By between 0.35 and 0.60 it meant that all hundredth, tenth and integer unit amounts within the range are specifically disclosed as part of the invention. Thus, 0.35, 0.36, 0.37 . . . 0.58, 0.59 and 0.6 unit amounts are included as embodiments of this invention.

In another embodiment of the invention, the polyethylenimine segments of the random copolymer comprise at least 85%, 80%, 75% or 70% of secondary amine.

In another embodiment of the invention, the composition further comprises a nucleic acid. The nucleic acid may be a small interfering RNA (siRNA).

Further in another aspect, the invention relates to a method of delivering a nucleic acid into a cell in vivo comprising exposing the cell to an effective amount of a composition comprising a nucleic acid as aforementioned in vivo.

Yet in another aspect, the invention relates to a method of delivering a nucleic acid into a cell in an animal in need thereof, in which the method comprises administering to the animal a composition comprising a nucleic acid as aforementioned in an amount sufficient to expose the cell in the animal to an effective amount of the composition comprising the nucleic acid.

In another embodiment of the invention, the cell is a cancer cell and the nucleic acid is a small interfering RNA (siRNA).

In another embodiment of the invention, the polyethylenimine of the random copolymer comprises at least 80% of secondary amine.

In another embodiment of the invention, the polyethylenimine of the random copolymer comprises at least 85% of secondary amine.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

1. Monomers and Reagents

Ethylene diamine ($M_1$) and ethanolamine ($M_2$) were purchased from Sigma-Aldrich and Riedel-de Haen, respectively. No purification was performed prior to use. The commercial BPEIs (1.8 kDa, 50 wt. % solution in water) and Lipofectamine (Lipofectamine™ 2000 reagent, 1 mg/mL) were purchased from Aldrich and Invitrogen, respectively.

2. Synthesis of LPEI-co-PEG ($P_2$)

To synthesize $P_2$, 100 μL of $M_2$ was added to 5 mL of water (18 MΩ cm$^{-1}$) and then the mixture was irradiated with synchrotron X-rays (4-30 keV, $10^5$ Gy/s) at room temperature for 5 min. The final products were lyophilized to remove any remaining monomer.

3. Basic Analysis of $P_2$

LPEI-co-PEG ($P_2$) was characterized by $^1$H NMR, $^{13}$C NMR, FT-IR and elemental analysis. $^1$H NMR and $^{13}$C NMR spectra, FT-IR spectra and elemental analysis data were collected using a Varian 400MR, Jasco FT/IR-4200, and an Elementar vario EL III, respectively. The optical spectra were measured using a Varian Cary 50 UV/V is spectrophotometer and a Varian Cary fluorescence spectrophotometer. To estimate the percentage of secondary amines in $P_2$, 0.011 g of the copolymer was dissolved in 20 mL of 1:1 isopropyl alcohol: ethylene glycol mixture. After mixing, either acetic anhydride (0.2 mL) was added to block all primary amines and secondary amines or salicylaldehyde (0.2 mL) was added to only block primary amines. After reacting for 30 minutes, the two solutions were titrated with 0.01N HCl, respectively.

4. Cell Culture

Human lung cancer cell lines such as A549, H460 and human breast cancer cell line (MDA-MB-231) were cultured in a humidified atmosphere with 5% $CO_2$. A549 cells were cultured in DMEM (Gibco, NY, USA); H460 cells and MDA-MB-231 cells were cultured in RPMI 1640 medium (Gibco, NY, USA), supplemented with 10% fetal bovine serum (FBS; Gibco, NY, USA) and 1% penicillin/streptomycin (P/S; Gibco, NY, USA).

5. Intracellular Imaging by Confocal Microscope

Cells were seeded at a density of $1\times10^5$ cells per well in μ-Dish (35 mm, ibidi, Germany) for 24 h. The cells were treated with $P_2$ (100 ng/ml) for 1.5 h and washed to remove the $P_2$-containing medium. A fresh medium containing 100 nM LYSO TRACKER® Red (Molecular Probes for labeling and tracking acidic organelles in live cells) and 100 nM DAPI (or 4',6-diamidino-2-phenylindole, which is a fluorescent stain that binds strongly to DNA and is a nucleus-specific dye; Invitrogen, USA) was added into the dish. After 5 min, the incubation medium was aspirated, and cells were washed three times with saline. The washed cells were observed in serum-free medium with a confocal laser scanning microscope at 532 nm and 473 nm, the excitation wavelengths for LysoTracker Red and $P_2$, respectively. Long-pass filters of 590 nm and 510 nm were used to detect red and green fluorescence, respectively. Confocal images were captured with a confocal spectral microscope (Olympus FV 10i) using a 60× oil immersion objective.

6. MTT Assay

The proliferation of A549 and H460 cells in the presence of various concentrations of $P_1$ and $P_2$, was determined using 3-(4,5-dimethylthiazol-2-yl)-2,5-diphenyl tetrazolium bromide (MTT assay, Sigma, MO, USA). A549 and H460 cells were seeded into 24-well plates at a density of $1\times10^5$ cells/well, respectively. The cells were treated with either $P_1$ or $P_2$ and incubated at 37° C., 5% $CO_2$ for 48 h. After removal of the supernatant of the cell culture medium, the cells were incubated with MTT at 37° C. for 1 h. After treatment, the formazan product from MTT was dissolved in DMSO and quantified using a conventional ELISA reader at 450 nm.

7. LDH Assay

Lactate dehydrogenase (LDH) leakage was measured to determine any acute membrane disturbance using an LDH kit (Promega, USA). LDH is a marker of cytotoxicity. To test $P_1$ and $P_2$ $1\times10^5$ cells were plated in 24-well tissue culture plates, incubated overnight and then treated with the individual polymers up to 48 hours. The supernatant (50 μL) from cell culture was collected and transferred to 96-well plates, into which a solution of 50 μL of LDH assay substrate was added. After incubation for 30 min at room temperature, LDH in the treated cells was quantified using an ELISA plate reader at 490 nm.

8. Evaluation of the Protection and Release of siRNA by $P_2$

Loading solutions were loaded onto the tank of agarose gel before separation. The total volume of each loading solution was 25 μL in pH 7.4 PBS, in which each loading solution comprises a complex solution and a buffer solution. The complex solution comprises siRNA (1.875 μL, 40 μg/150 μL) and $P_1$ or $P_2$ (10 μg/μL) of various volumes ranging from 0.5 μl to 4.5 μL and glycerol. Electrophoresis was carried out at a voltage of 100 V (MP-250V Power Supply, Major Science) for 15 min in TBE running buffer solution [0.5× TBE (5.4 g Tris/HCl, 2.75 g boric acid and 0.37 g EDTA dissolved in 1 L MilliQ water, pH 7.0)]. Multi-images were detected by an imaging system (FLUORCHEM® FC2, Alpha Innotech).

9. siRNA/$P_2$ Complexes Gene Silencing Detected by Flow Cytometry

MDA-MB-231 cells (breast cancer cell line) with GFP plasmid were seeded on a 24-well plate at a cell density of $1\times10^5$ cells/well 1 day before siRNA/$P_1$($P_2$) complexes (N/P=70) treatment.

After 48 h, cells were rinsed with trypsin solution (Biological Industries), incubated at 37° C. for 4 min and then added 5 mL of medium containing 10% FBS. After spinning down, the cells were washed with PBS solution twice and then diluted with 1 ml of PBS. Cells were analyzed on a BD FACSCAN™ analyzer (Becton-Dickinson, San Jose, Calif.) using WinMDI 2.9 analysis software; data from 10,000 events were collected for further analysis. The sense and antisense of the anti-GFP siRNA hairpin transcript were 5'-GGCAAGCUGACCCUGAAGUUCUUTT-3' (SEQ ID NO: 1) and 5'-AAGAACUUCAGGGUCAGCUUGCCTT-3' (SEQ ID NO: 2), respectively.

10. In Vivo Tumor Treatment with VEGF siRNA/$P_2$ Complex

To establish the tumor model for in vivo tumor treatment therapy experiments, $3\times10^6$ cells/well of MDA-MB-231 was suspended in RPMI serum-free medium and then an aliquot (50 μL) of the MDA-MB-231 was subcutaneously injected into the 6-/7-week-old male nude mice. Tumor size was measured using a vernier caliper across its longest (a) and shortest (b) diameters, and its volume was calculated by using the formula of $V=0.5a\times b^2$. Tumor was treated by three samples including saline (control), $P_2$ alone and anti-VEGF siRNA/$P_2$ complexes, respectively, when the tumor size became approximately 50 mm$^3$. Each nude mouse was treated with the individual sample via intra-tumor injection three times. The interval of each injection was 3 days. Anti-VEGF siRNA was purchased from Bioneer Co. (Daejeon, Korea). The sense- and antisense-VEGF siRNA were 5'-UGAAGAUGUACUCGAUCUCAUCAGGTT-3' (SEQ ID NO: 3) and 5'-CCUGAUGAGAUCGAGUACAUCUUCATT-3'

(SEQ ID NO: 4). Tsai et al. "A single-monomer derived Linear-like PEI-co-PEG for siRNA delivery and silencing" *biomaterials* 2011, 32, 3647-3653 (in press), which is incorporated herein by reference in its entirety.

Results and Discussion

1. Characterization of $P_2$

Figure 2:
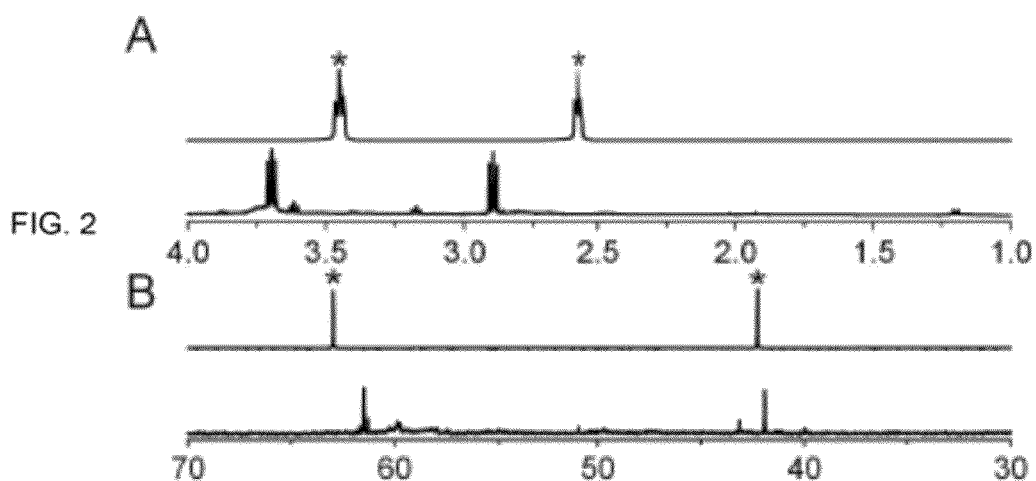

After completion of the polymerization of ethanolamine ($M_2$), $^1H$ NMR spectrum (FIG. 2A) shows two sets of triplet peaks at 2.89 ppm and 3.70 ppm that can be assigned as the —$CH_2CH_2NH$— and the —$CH_2CH_2O$— signal of the ethyleneimine and ethylene glycol units, respectively. Further characterization of $P_2$ by $^{13}C$ NMR combined with DEPT, FIG. 2B shows that two peaks of $M_2$ at 42.3 and 63.0 ppm disappeared, and several new peaks appearing at 41.9, 43.1, 59.9 and 61.5 ppm were assigned to the methylene groups neighboring the polymer amine and ether moieties, indicative of the formation of a copolymer of PEI and PEG segments (denoted by LPEI-co-PEG, $P_2$).

Figure 3:
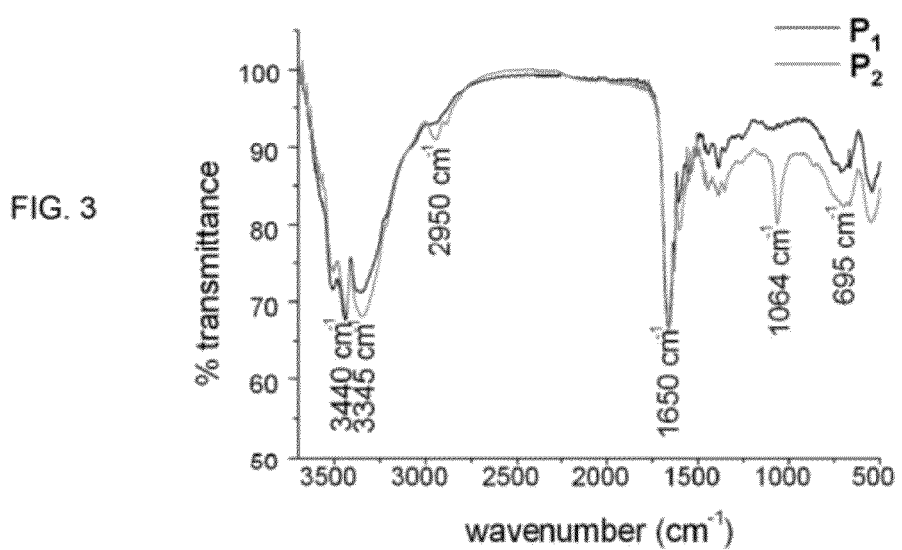
FIG. 3 shows FT-IR transmittance spectra of $P_1$ and $P_2$. Characteristic assignments: N—H stretches of secondary amine ($R_2NH$) and primary amine ($RNH_2$) located at 3445 $cm^{-1}$ and 3345 $cm^{-1}$, respectively. N—H bending vibration located at 1650-1580 $cm^{-1}$. N—H wags located at 910-665 $cm^{-1}$. C—O stretch appeared at 1064 $cm^{-1}$.

Similar results were obtained via FT-IR measurements; FIG. 3 shows a transmission IR spectrum of lyophilized $P_2$ (black line) prepared in a KBr pallet. The two bands appearing at 3440 and 3345 $cm^{-1}$ were assigned to the stretching mode of primary amines, which was expected for the terminal group of $P_2$. The stretching mode of secondary amines also was observed in the same absorption region (3500-3300 $cm^{-1}$), but no discernible difference between primary and secondary signals was observed. The peaks at 2938 and 2850 $cm^{-1}$ represent $\upsilon_a(CH_2)$ and $\upsilon_s(CH_2)$, respectively, illustrating the presence of methylene groups in $P_2$. The $P_2$ spectrum (gray line) was very similar to that of $P_1$ (black line) synthesized by $M_1$, but only $P_2$ exhibited a band at 1064 $cm^{-1}$ that was attributable to a $\upsilon_{str}(CO)$, indicating that the presence of C—O bonds from PEG. The weight-averaged molecular mass ($M_w$) and molecular conformation were estimated by size-exclusion chromatography coupled with multi-angle light scattering (SEC-MALS). The $M_w$ of $P_2$ was 1.2-1.3 kDa with a polydisperisty index (PDI) of 1.14±0.44. To calculate elemental analysis data, the ratio of oxygen/nitrogen of the polymer was 0.46, indicating that $P_2$ was indeed a copolymer containing both PEI and PEG segments. The composition of secondary and tertiary amine of $P_2$ was confirmed by potentiometric titration, as described in Materials and Methods section. After being calculated, the ratio of between secondary and tertiary amine for $P_2$ was 6.5:1. This means that the PEI portions of $P_2$ (87%) were mostly linear similar to the 90% secondary amine of $P_1$ estimated previously. The polymerization parameters and characterization data for the compositions $P_1$ and $P_2{}^a$ are summarized in Table 1.

TABLE 1

| denotation | reaction time (min) | yield (%) | $M_n{}^b$ (kDa) | $M_w{}^b$ (kDa) | $PDI^b$ | 2°-$N^c$ (mole %) | ratio of O/N $(mol/mol)^d$ |
|---|---|---|---|---|---|---|---|
| $P_1$ | 5 | 17 | 0.91 | 1.37 | 1.51 | 90 | 0 |
| $P_2$ | 5 | 21 | 1.11 | 1.28 | 1.16 | 87 | 0.46 |

Figure 4:
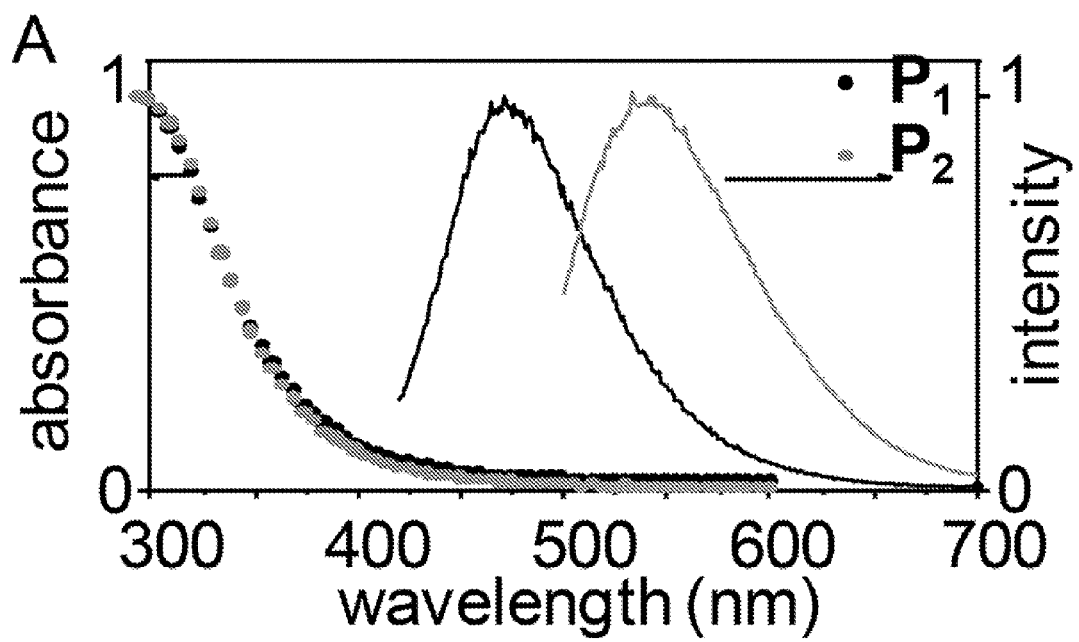
Figure 4:
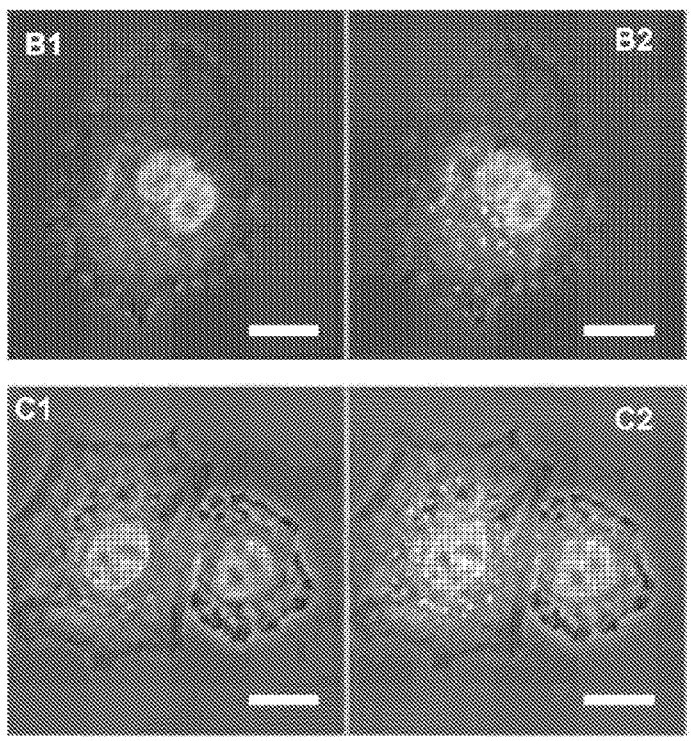

$^a$The reaction temperature was 25° C. (room temperature).
$^b M_n, M_w,$ and PDI were determined by multi-angle light scattering in water.
$^c$Secondary amine percentages of the PEI segment were confirmed by potentiometric titration.
$^d$The weight percentage of oxygen atoms as measured by elemental analysis 2. Optical Properties of $P_2$ During polymerization by synchrotron radiation, the color of the aqueous solution gradually changed from colorless to pale-yellow. The optical properties of $P_2$ were explored and compared to those of $P_1$. FIG. 4A displays the absorption and emission spectra of $P_1$ (black line) and $P_2$ (gray line) with a broadening band from 250 to 450 nm and an emission maximum appearing at approximately 540 nm (10 mg/mL of $P_2$). The quantum yield and lifetime of $P_2$ were 2% and 3.1 ns, respectively. The photoluminescence may be attributed to the incorporation effect between oxygen in the solution and nitrogen atoms of the polymer. FIG. 4B shows the intense green photoluminescence in the cytoplasm, localized to the endosome and/or lysosome after uptake, indicating that $P_2$ was able to cross the cell membrane with positive charges, which is consistent with the previous result.

3. Biosafety of LPEI-co-PEG ($P_2$)

Figure 5:
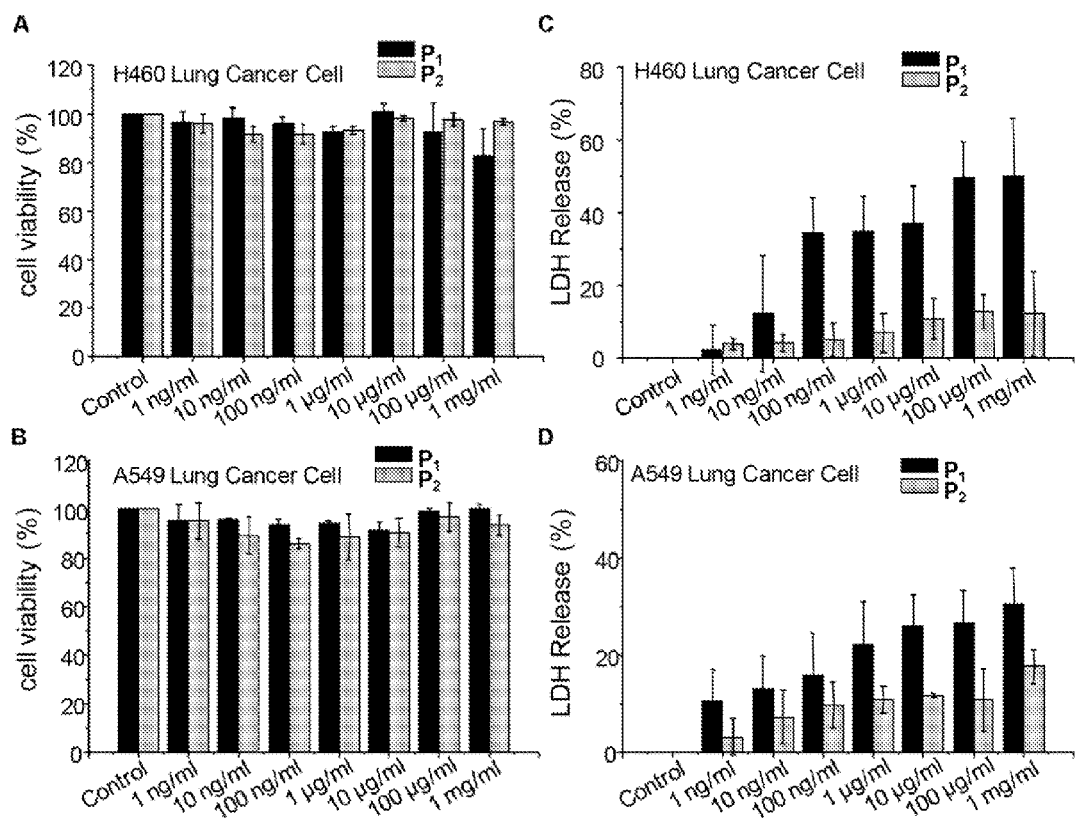
FIGS. 5A-5D are plots showing results from MTT (A and B) and LDH (C and D) assays for H460 and A549 cells, respectively. Both cell lines were treated with either $P_1$ or $P_2$ at different concentrations ranging from 1 ng/mL to 1 mg/ml.

The biosafety of the copolymer LPEI-co-PEG ($P_2$) was examined by measuring 3-[4,5-dimethylthiazo-2-yl]-2,5-diphenyltetrazolium bromide (MTT) reduction and LDH leakage, and the results were compared to those of the $P_1$ and commercial BPEIs. FIGS. 5A and 5B show that cell viabilities of H460 and A549 cells, respectively. Cells were incubated in various concentrations of $P_1$, $P_2$ and BPEIs for 48 h. Much less cell death (85% cell viability compared with control) was observed in cells treated with $P_1$ compared with that of commercial BPEIs (25% cell viability compared with control, data not shown). No significant cell death (96% cell viability compared with control) was observed in cells treated with $P_2$ even at a high concentration (1 mg/mL). The significant difference (10%) in cell viability between $P_1$ (data not shown) and $P_2$ may not be relevant in vitro but could limit the in vivo applications of $P_1$. MTT can measure mitochondrial activity, but can not recognize cell membrane damage. For further verifying cell damage, a LDH assay was used to verify the biosafety of $P_1$ and $P_2$. An increase in the concentration of $P_1$ led to a dramatic increase in cell death. As shown in FIGS. 5C and 5D, at the highest concentration tested more than 40% and 50% LDH release were observed for A549 and H460, respectively. Conversely, LDH levels increased less than 10% and 20% for H460 and A549, respectively, after cell treatment with $P_2$, which illustrates its higher biosafety than $P_1$.

Figure 6A:
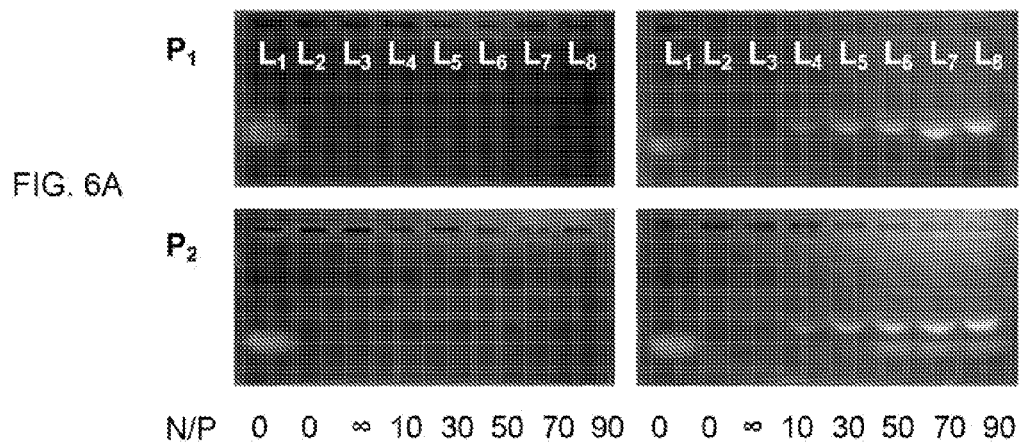
FIG. 6A shows results of gel electrophoresis analysis. Left panel: the agarose gel electrophoresis of siRNA/$P_1$ (or $P_2$) complexes at various N/P ratios (w/w). Right panel: protection and release studied of siRNA. After RNase digestion, 1 μL of SDS (10%) was added to dissociate siRNA from the complexes. The results showed siRNA was released from $P_2$ (not observed from $P_1$). The "N" stands for the amine-containing copolymer ($P_1$ or $P_2$) and the "P" stands for the phosphate-containing siRNA. The ratio of N/P represents the ratio of the copolymer ($P_1$ or $P_2$) to siRNA by weight.
Figure 6B:
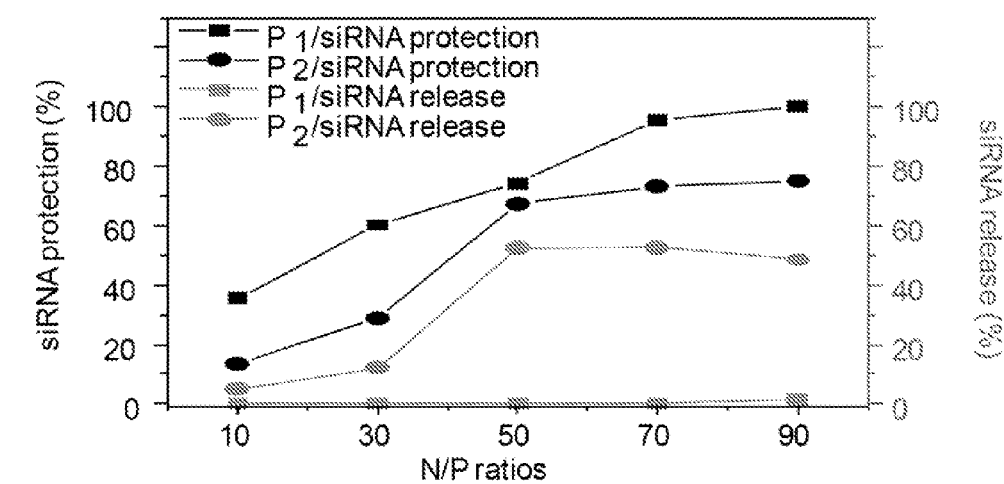
FIG. 6B is a graph showing siRNA protection and release from siRNA/$P_1$ (or $P_2$) complexes at various N/P ratios.
Figure 7:
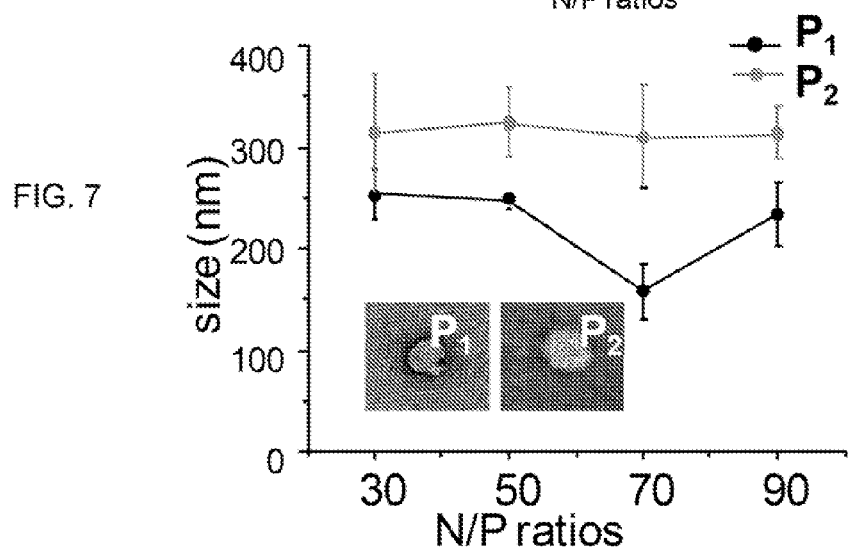
FIG. 7 shows size distribution of complexes with various N/P ratio measured by DLS. Inset figures: TEM photographs of two complexes at an N/P ratio of 70. The sample (1 μL, 10 mg/mL) was deposited on the carbon coated grid and stained with 2% uranyl acetate.

4. Stability Study and Release Comparison Between siRNA/P and siRNA/$P_2$ Polyplexes The siRNA was associated with $P_1$ and $P_2$, respectively, at various ratios (w/w) of amine/phosphate (N/P) before conducting stability and release studies. The stabilities of siRNA/$P_1$ and siRNA/$P_2$ complexes were examined by RNase digestion to mimic physiological conditions. Free siRNA (FIG. 6A, upper and lower left panel, lane 1) was detected with ethidium bromide stain after running agarose gel electrophoresis. Once siRNA was either digested by RNase (FIG. 6A, upper and lower left panel, lane 2) or completely bound by polymers (FIG. 6A, upper and lower left panel, lanes 4-8), the ethidium bromide fluorescence disappeared. FIG. 6A (left panel, lanes 4-8) represented two complexes with N/P ratios ranging from 10 to 90 that prevented RNase digestion, which indicated protection of siRNA via $P_1$ and $P_2$ association. The lane 3 in FIG. 6A left panel presents only either P1 or P2 without containing siRNA. The siRNA release properties of these complexes were further studied by treatment with SDS after RNase digestion. FIG. 6A upper right panel shows no detectable ethidium bromide signal, indicating that siRNA was not released from the siRNA/$P_1$ complexes. In contrast, a pronounced fluorescence signal (FIG. 6A, lower right panel) was visible for the siRNA/$P_2$ complexes by SDS-replacement after resisting the RNase digestion, indicating that the siRNA could more easily dissociate (52%, an N/P ratio of 70; right panel, gray circle) from the siRNA/$P_2$ complexes compared to that (<5%, an N/P ratio of 70; right panel, gray square) from the siRNA/$P_1$ complexes. The interaction between siRNA and $P_2$ was reduced to 75% at the presence of PEG segments (an N/P ratio of 70; FIG. 6B, black circle) compared to $P_1$ (an N/P ratio of 70; FIG. 6B, black square) without affecting the siRNA stability, which might be enhanced through effective RNase-resistance of PEG. DLS and TEM measurements (FIG. 7) demonstrated that the hydrodynamic diameters of siRNA/$P_1$ and siRNA/$P_2$ were significantly different. The size of siRNA/$P_1$ complexes ranged from 150 nm to 250 nm, which is smaller than the 300-350 nm range of siRNA/$P_2$ complexes. The results suggest that the PEG segments of $P_2$ can compensate the association force between PEI and siRNA, resulting in the formation of looser structures in the siRNA/$P_2$ complexes.

5. Enhanced Transfection Efficiency by the siRNA/$P_2$ Complexes

Figure 8:
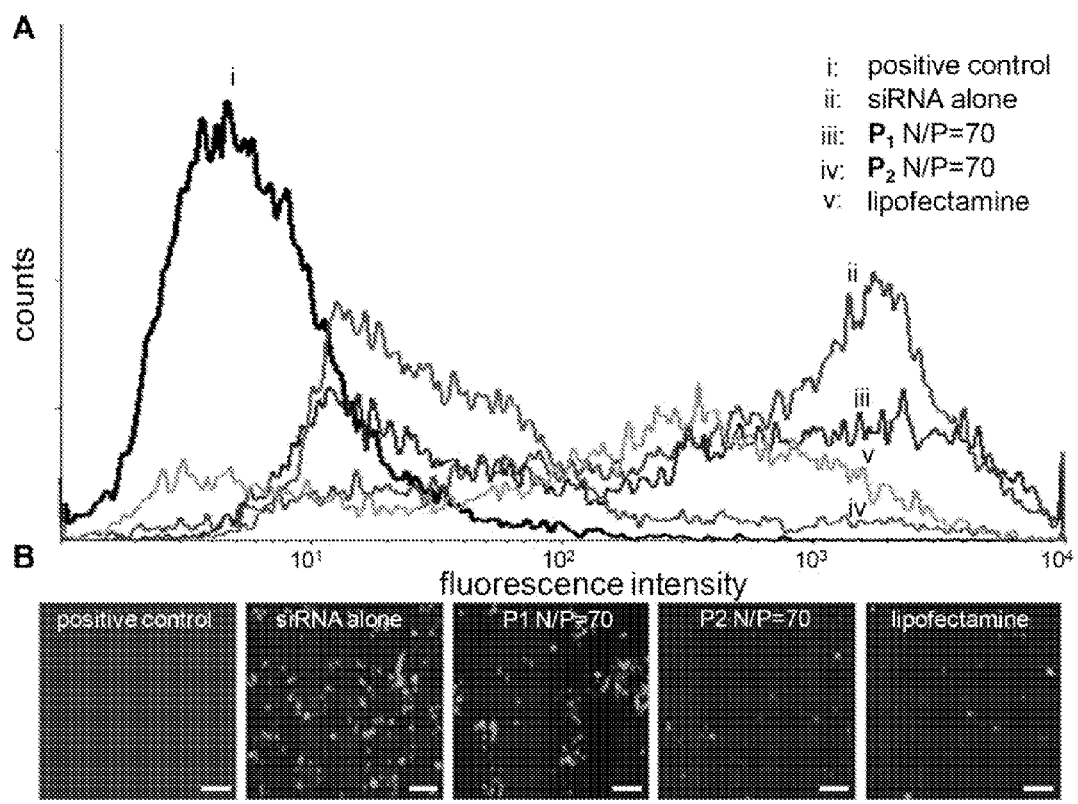
FIGS. 8A-8B show results of evaluations of GFP knockdown in three sets of complexes performed in GFP-MDA-MB-231 cells.

To further investigate the performance of siRNA transfection efficiency in vitro, P2 was associated with anti-GFP siRNA (siGFP) to form a complex for treating with cells. For comparison, two control experiments such as the $P_1$ and Lipofectamine (a commercial transfection agent) complexes were run in parallel. MDA-MB-231 cells over-expressing GFP were employed to perform GFP knockdown by siGFP. The siGFP/$P_2$ complexes with N/P ratios ranging from 10 to 90 were analyzed by flow cytometry to evaluate the efficiency of gene silencing and these ratios were compared with those of siGFP/$P_1$ and siGFP/Lipofectamine complexes. No significant difference in fluorescence signal was observed in cells treated with the siGFP/$P_2$ complex with N/P ratios from 10 to 50 (data not shown). Conversely, a noticeable GFP protein knockdown (line iv, 75% fluorescence decrease compared to siRNA alone, line ii) in cells treated with the siGFP/$P_2$ complexes at an N/P ratio of 70 was observed (FIG. 8A). This rate was higher than those of the siGFP/$P_1$ complexes (line iii, only 19% fluorescence decrease compared to siRNA alone, line ii) and the siGFP/Lipofectamine complexes (line v, only 20% fluorescence decrease compared to siRNA alone, line ii). The corresponding images were shown in FIG. 8B, the results illustrate that the silencing efficiency of siGFP/$P_2$ complexes was indeed higher than that of the siGFP/$P_1$ complexes. The positive control (line i) refers to the MAD-231 cells without emitting fluorescence, instead of the MDA-231 cells over-expressing GFP. The numbers in the x-axis of FIG. 8A represent the fluorescent intensity, and the counts in y-axis represent the number of cells.

6. The Suppression of Tumor Growth by the siRNA/$P_2$ Complexes

Figure 9:
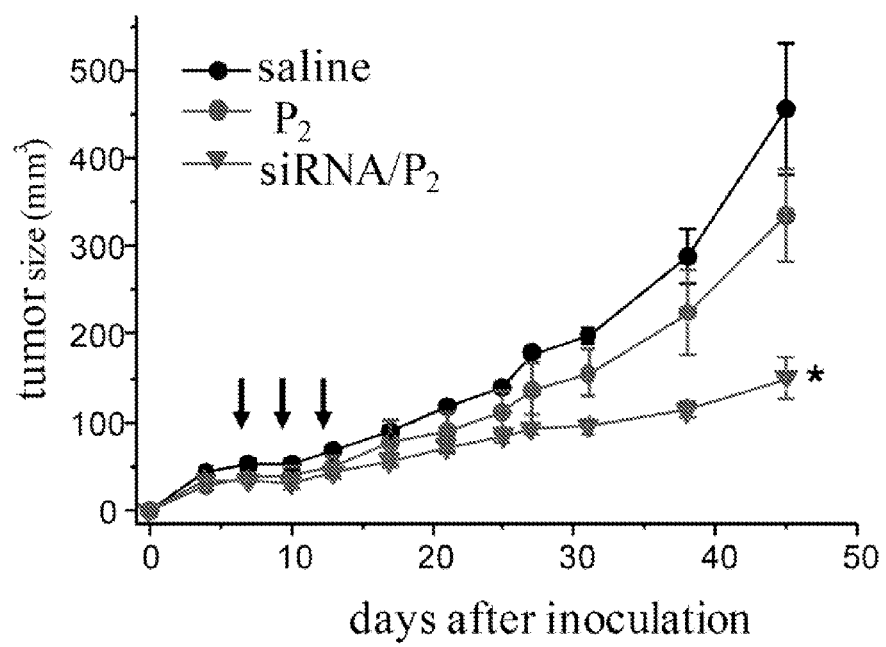
FIG. 9 shows anti-tumor therapeutic effects of siRNA/$P_2$ complex in nude mice inoculated with MDA-MB-231 cells for tumor growth. Mice were intra-tumor administered three times on days 7, 10, 13 (arrows) with 50 μL of the siRNA/$P_2$, $P_2$ alone or with saline alone (n=3 in each group). *P<0.05 versus saline control on day 45.

To further verify whether the efficient gene silencing would be applicable in vivo, siRNA/$P_2$ complexes were utilized to directly silence the mRNA of VEGF for suppressing tumor growth. VEGF is a well-known protein in stimulating the development of new blood vessels (angiogenesis) during tumor growth. In the experiment, siRNA with anti-VEGF function was associated with $P_2$ to prevent it from being digested by RNase, and then the siRNA/$P_2$ complex was injected to tumor. A significant suppression (FIG. 9) in the tumor growth was observed in mice treated with the siRNA/$P_2$ complexes compared with other control groups ($p<0.05$). The results indicated that the LPEI-co-PEG was able to sufficiently deliver siRNA to suppress tumor growth.

CONCLUSIONS

The invention relates to a single-monomer derived LPEI-co-PEG as an efficient vehicle for siRNA delivery and target-specific gene silencing both in in vitro and in vivo. The copolymer LPEI-co-PEG was synthesized by intensive synchrotron X-ray irradiation from ethanolamine ($M_2$) in the absence of any catalyst and organic solvent. The incorporation of PEG segments into the copolymer $P_2$ not only solved the cytotoxicity problems, but also improved the efficiency of siRNA release compared to either LPEI ($P_1$) or Lipofectamine. This single-monomer derived copolymer LPEI-co-PEG was synthesized by a facile and high throughput strategy that will be useful in future biological applications.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of synthesizing a random copolymer of polyethyleneimine and poly(ethylene glycol), comprising:
exposing, ethanolamine in a solution to electromagnetic radiation for a sufficient time to polymerize the ethanolamine ($OHCH_2CH_2NH_2$) and result in formation of the random copolymer comprising polyethyleneimine and poly(ethylene glycol), wherein the polyethyleneimine comprises ethyleneimine ($—CH_2CH_2NH—$) units and the poly(ethylene glycol) comprises ethylene glycol ($—CH_2CH_2NH—$) units, and the polyethylenimine has a linear backbone; and
removing, remaining ethanolamine after the formation of the random copolymer.

2. The method of claim 1, wherein the ethanolamine in the solution is exposed to the electromagnetic radiation for no greater than 10 minutes.

3. The method of claim 1, wherein the random copolymer is formed in the absence of organic solvents, acids, and catalysts.

4. The method of claim 1, wherein the electromagnetic radiation is selected from the group consisting of X-rays, microwaves, and gamma-rays.

5. The method of claim 1, wherein the radiation comprises energy of 3 to 3,000 KeV and a radiation dose of from $2\times10^3$ to $10^7$ Gy/s.

6. The method of claim 1, wherein the electromagnetic radiation comprises X-rays.

7. The method of claim 1, wherein the random copolymer is free of peptide.

8. The method of claim 1, wherein the random copolymer has a weight average molecular weight ranging from 1 kDa to 200 kDa.

9. The method of claim 1, wherein the random copolymer has a polydisperisty index of greater than 1 hut less than 1.9.

10. The method of claim 1, wherein the random copolymer has an oxygen/nitrogen ratio of between 0.35 and 0.60.

11. The method of claim 1, wherein at least 70% of the amino groups in the polyethylenimine of the random copolymer are secondary amines.

12. The method of claim 1, wherein at least 80% of the amino groups in the polyethylenimine of the random copolymer comprise at least 80% of are secondary amines.

13. The method of claim 1, wherein at least 85% of the amino groups in the polyethylenimine of the random copolymer are secondary amines.

14. A method of preparing a composition comprising a random copolymer, comprising:
exposing ethanolamine in a solution to electromagnetic radiation for a sufficient time to polymerize the ethanolamine ($OHCH_2CH_2NH_2$), and result in formation of the composition comprising the random copolymer, wherein the random copolymer comprises polyethyleneimine and poly(ethylene glycol), the polyethyleneimine comprising ethyleneimine ($—CH_2CH_2NH—$) units and having a linear backbone, and the poly(ethylene glycol) comprising ethylene glycol ($—CH_2CH_2O—$) units; and
removing remaining ethanolamine after the formation of the random copolymer.

15. The method of claim 14, further comprising:
causing the random copolymer to form a complex with a nucleic acid.

16. The method of claim 15, wherein the nucleic acid is a small interfering RNA (siRNA).

17. The method of claim 14, wherein at least 70% of the amino groups in the polyethylenimine of the random copolymer are secondary amines.

18. The method of claim 14, wherein the random copolymer has a weight average molecular weight ranging from 1 kDa to 200 kDa.

19. A method of synthesizing a random copolymer of polyethyleneimine and poly(ethylene glycol); comprising:

provifing a mixture comprising ethanolamine and water;

exposing the mixture to X-ray radiation for a sufficient time to polymerize the ethanolamine ($OHCH_2CH_2NH_2$) and result in formation of the random copolymer comprising polyethyleneimine and poly(ethylene glycol), wherein the polyethyleneimine comprises ethyleneimine ($—CH_2CH_2NH—$) units and the poly(ethylene glycol) comprises ethylene glycol ($—CH_2CH_2O—$) units, and the polyethylenimine has a linear backbone.

20. The method acclaim 19, further comprising lyophilizing the mixture after exposing the step.

\* \* \* \* \*